United States Patent [19]

Holbrook et al.

[11] Patent Number: 4,614,572

[45] Date of Patent: Sep. 30, 1986

[54] LIQUID PHASE CHLORINATION OF CHLORINATED METHANES

[75] Inventors: Michael T. Holbrook, Baton Rouge, La.; Thomas E. Morris, Lake Jackson, Tex.

[73] Assignee: The Dow Chemical Company, Midland, Mich.

[21] Appl. No.: 752,696

[22] Filed: Jul. 8, 1985

[51] Int. Cl.$^4$ .................... B01J 19/12; C07C 17/00
[52] U.S. Cl. ...................... 204/157.95; 570/252; 570/253
[58] Field of Search .............. 204/158 HA, 163 R; 570/252, 253

[56] References Cited

U.S. PATENT DOCUMENTS 3,502,734  3/1970  Baird et al. .................. 570/252

FOREIGN PATENT DOCUMENTS 0005296  11/1979  Belgium ........................ 570/253
13210    1/1980   Japan .......................... 204/163 R
55-043002 3/1980  Japan .
142927   9/1982   Japan .......................... 204/163

OTHER PUBLICATIONS

Hydrocarbon Processing; S. Akiyana et al; "Chloromethanes From Methanol", Mar. 1981; pp. 76-78.

Primary Examiner—Howard S. Williams
Attorney, Agent, or Firm—A. J. Young

[57] ABSTRACT

This invention relates to an improved liquid phase chlorination process for the chlorination of methyl chloride to preferentially produce methylene chloride. The chlorine is provided to the reaction mixture in a mole percent, based upon the total moles of chlorine and methyl chloride in the mix, which ranges from about 16 mole percent to about 2 mole percent.

5 Claims, 1 Drawing Figure

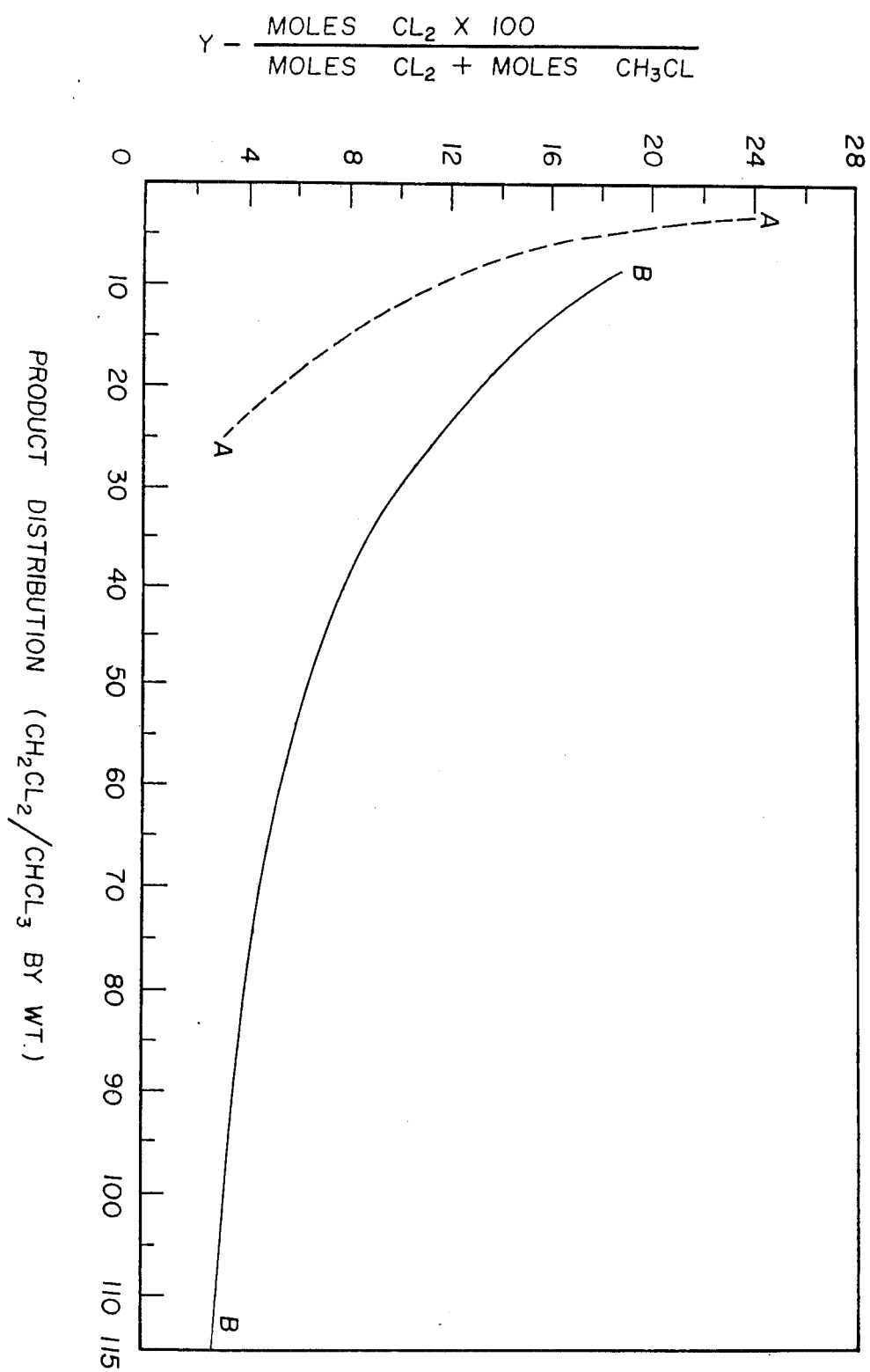

LIQUID PHASE CHLORINATION OF CHLORINATED METHANES

BACKGROUND OF THE INVENTION

This invention relates to an improved process for the chlorination of chlorinated methanes. More particularly, the process of this invention provides for reacting chlorinated methanes and chlorine in a liquid phase environment and in such relative amounts to yield a highly selective product distribution.

The gas phase reaction of chlorine and methyl chloride, methylene chloride and chloroform, is well known in the prior art. The reaction occurs at elevated temperatures i.e., 400° C.-600° C., and at about atmospheric pressure. While gas phase chlorination has been widely used it has several serious drawbacks, some of which are directly related to the required process conditions.

Due to the high temperatures required, side reactions are probable. The most troublesome of the side reactions are those which produce both saturated and unsaturated carbon to carbon bonding. Unsaturated carbon to carbon bonding produces chlorocarbons, such as, vinylidene chloride, tran— and cis—dichloroethylene and trichloroethylene. These unsaturated compounds contaminate the product thereby requiring additional equipment and energy consumption to effect their removal from the product. The high process temperatures can also result in the production of tar and carbon which cause equipment fouling.

Further, with the gas phase reaction, unreacted methyl chloride must be separated and recycled back to the reactor. This recycle requires a compressor and such compressors are not only expensive but are generally troublesome to keep in service.

Even further, the gas phase reaction does not yield highly selective product distribution when the production of methylene chloride is desired. For example, the typical gas phase reaction produces a methylene chloride to chloroform weight ratio of from about 3 to about 25 depending upon the amount of chlorine fed.

In Japanese Patent Application, Kokai Patent No. 55043002 (published Mar. 26, 1980) it is reported that the liquid phase reaction of chlorine and chlorinated methane obviates some of the drawbacks which are characteristic of the above discussed gas phase reaction. The reported liquid phase reaction is run at low temperature, i.e. 60° C. to about 150° C., and at pressure from about 100 psig to about 430 psig. The low reaction temperature avoids or at least lessens the production of carbon-carbon bonding. The high pressure allows for more economical product separation and eliminates the need for a methyl chloride recycle compressor.

Despite these benefits for this reported liquid phase reaction it is not shown to provide highly selective product distribution when used to produce methylene chloride even though its product distribution is slightly better than that which is obtainable with the gas phase reaction. For example, the reported liquid phase reaction is shown to provide a methylene chloride to chloroform weight ratio which ranges from about 0.4 to 4 depending on the amount of chlorine fed to the reaction.

It is therefore an object of this invention to provide a liquid phase reaction of chlorine and chlorinated methane which is capable of providing high selectivity in product distribution when methylene chloride is the desired product.

THE INVENTION

The highly selective production of methylene chloride is made possible by the process of this invention. The process comprises providing a liquid reaction mix of methyl chloride and chlorine which mix initially has chlorine in an amount within the range of from about 3 to about 16 mole percent based upon the initial total amount of chlorine and methyl chloride in said mix.

The resultant chlorination reaction occurs in a reaction vessel maintained at high pressure, within the range of from about 100 to about 800 psig. The reaction mix is maintained at a temperature within the range of from about 40° C. to about 175° C.

By providing the chlorine reactant in the above mentioned amounts to the reaction mix it has unexpectedly been found that the production of methylene chloride is highly favored over the production of chloroform—indeed the resultant products from the process of this invention have been found to have a weight ratio of methylene chloride to chloroform of 115. Such a high selectivity for the production of methylene chloride occurred with a reaction mix containing 87 weight % methyl chloride and 3.56 weight % chlorine (2.82 mole % chlorine based on methyl chloride and chlorine only). The presence of carbon tetrachloride in this reaction mix was quite low i.e. 9.44 weight percent.

The chlorination process of this invention may be either initiated or uninitiated. The benefit of initiation is that the process time can be substantially reduced. However, the various initiator compounds known to the prior art add costs to the process and thus the reaction time saved must be weighed against the costs. Also, initiator compounds generally will form decomposition products which will require removal from the reaction vessel as bottoms or which may result in production of water in the reaction system causing corrosion problems. Further, these decomposition products may complete with the methyl chloride for the available chlorine in the reaction mix. Initiation with ultraviolet light avoids the problems of initiator compounds but involves the use of vessel light ports or fiber optics to allow entry of the ultraviolet light into the reaction vessel. The high pressures used by the process of this invention could make the reaction vessel design difficult and costly so as to provide the required ultraviolet light entry structures.

The methyl chloride, chlorine, initiator compound and any solvent used in the process of this invention should be substantially free of contamination. It is important that the presence of dissolved iron, oxygen and water be kept to a minimum as such contaminants adversely affect the reaction rate. Preferably the oxygen and the dissolved iron content should be less than 1 ppm each, while the water content should be less than 20 ppm. The oxygen will most likely be introduced to the reaction mix if liquid chlorine is used as the chlorine portion of the reaction mix. Reduction of the oxygen content in the liquid chlorine can be achieved by conventional means.

The FIGURE is a graph of mole percent $Cl_2$ fed vs weight ratio of methylene chloride to chloroform produced for both a gas phase chlorination process and the liquid phase process of this invention.

The methyl chloride reactant used can be best provided by the vapor or liquid phase hydrochlorination of methanol with hydrochloric acid as is well known in the art. After removing the by products and drying, the methyl chloride product is liquified and ready for introduction into the reaction vessel.

The chlorine reactant is next charged to the reaction vessel, which vessel is kept at the before-mentioned 40° C. to about 175° C. temperature and 100 psig to about 800 psig pressure. The chlorine can be either introduced in liquid form, dissolved in a solvent such as carbon tetrachloride, or can be directly sparged as a gas into the methyl chloride reactant. If the chlorine is fed in liquid form, then, to prevent the existence of a possible explosion hazard, there should be provision for high and quick mixing of the chlorine into the methyl chloride.

As mentioned previously the mole percent of chlorine fed is based upon the total moles of chlorine and methyl chloride in the reaction mix and is preferably within the range of from about 2 mole percent to about 16 mole percent to obtain the high preferential production of methylene chloride over that of chloroform. In accordance with the process of this invention, such a quantitative relationship between the methyl chloride and chlorine reactants can yield a weight ratio of methylene chloride to chloroform ranging from about 13 for a 16 mole percent chlorine feed to about 115 for a 2.8 mole percent chlorine feed.

The process of this invention can be initiated by ultraviolet light or with initiator compounds. Exemplary of useful initiator compounds are: azobisisobutyronitrile; benzoyl peroxide; decanoyl peroxide; lauroyl peroxide; and 2-ethylhexyl peroxy-dicarbonate. Other compounds which have initiating azobisnitrile or peroxide groups may be used. An inorganic initiator is $F_2$, however, the possible generation of HF makes its use questionable from a corrosion standpoint.

The use of an initiator is beneficial for two reasons, the main one being a reduction in reaction time and the other one being the tolerance of the subject process for the presence of a greater amount of contaminants, e.g. iron, $O_2$, water etc., than is observed for the uninitiated process.

The initiator compounds are generally introduced to the reaction mix solubilized in a chlorinated methane solvent. The amount of initiator used is dependent on the reaction temperature, the reaction time desired and the effectiveness of the particular initiator compound used. The higher the initiator concentration, the shorter the reaction time, however, the short reaction time sought has to be balanced against the before described drawbacks of initiator compound decomposition products. It has been found that a good balance can be obtained, when the initiator is azobisisobutyronitrile and the reaction temperature is at about 100° C., by using in the reaction mix about 50 ppm of the nitrile based upon the available chlorine. The reaction time in such circumstances was about 15 minutes. Concentrations for other initiator compounds are best determined empirically for each set of process conditions.

The products produced by the process of this invention yield a two phase flow from the reaction vessel and will include hydrogen chloride, methyl chloride, methylene chloride, chloroform and carbon tetrachloride. The products can be separated in any conventional manner. For example, the two phase flow can be first fed to a separator column to split the hydrogen chloride from the balance of the products. The hydrogen chloride can then be recycled to a hydrochlorination reaction for the production of methyl chloride. The remaining products are then sent to a series of rectification columns for separation and purification. Separated methyl chloride is suitable for recycle back to the reaction vessel.

The following Examples illustrate preferred embodiments of the process of this invention and should not be construed as limiting the scope of the invention.

EXAMPLES

For all examples, a 1 liter stirred reaction vessel was provided which had feed and discharge lines admitted to its interior. The interior of the reaction vessel, transfer lines, valves etc. were coated with polytetrafluoroethylene. The stirrer blades and shaft were also so coated. It is believed that such coating would diminish or prevent the formation of the $CCl_3$ radical from the reaction of $CCl_4$ and the equipment metal. The $CCl_3$ radical will produce, in the presence of a hydrocarbon, $CHCl_3$ which is not the product sought. It is believed that the above coating will not be necessary for larger, commercial size process equipment as the ratio of the metal surface subject to attack to the volume provided is much smaller than is the case for the instant 1 liter reaction vessel of these Examples.

The reaction vessel was maintained at the desired reaction temperature by the use of an electrical heater built for Parr reactors.

$CCl_4$ when used in a particular example, was dried by passage through an activated molecular sieve. The dried $CCl_4$ was fed into a $N_2$ flushed tank. The $CCl_4$ was then sparged with $N_2$ for 15 minutes to remove any dissolved $O_2$. $Cl_2$ was then bubbled through the $CCl_4$ and pumped to the reaction vessel to obtain a chlorine concentration as per the following Table. The $CCl_4/Cl_2$ solution was introduced into the reaction vessel and brought to a temperature generally 10° C. to 50° C. above the desired reaction temperature. Liquid methyl chloride was then pressured in the reaction vessel. The reaction vessel was run at the pressures shown in the Table. Stirring of the resultant reaction mix was continuous. The reaction mix was cooled by the liquid methyl chloride introduction but was maintained at reaction temperature by the electrical heater. If the $Cl_2$ was not dissolved in $CCl_4$ it was sparged into the liquid methyl chloride in the reaction vessel. The liquid methyl chloride was constantly stirred during the sparging. Liquid samples were drawn from a display in the reactor into a Valco liquid sample valve with a 3 microliter sample size. The samples were injected into a HP 5710 gas chromatograph with a TC detector. A 12 foot fluorolube column was used to separate the products.

The chlorine used in the Examples was liquid chlorine containing less than 25 ppm oxygen.

TABLE

| Example No. | Temp. °C. | Pressure psig | Initiator | Initiator Amount[1] | $CCl_4$ wt %[2] | $Cl_2$ mole %[3] | $CH_2Cl_2/CH_2Cl_3$[4]* |
|---|---|---|---|---|---|---|---|
| 1 | 100 | 530 | AIBN[5] | 53 | 9.4 | 2.82 | 115 |
| 2 | 100 | 460 | — | 0 | 14.2 | 4.54 | 68.0 |
| 3 | 120 | 590 | — | 0 | 15.2 | 4.92 | 48.3 |
| 4 | 100 | 540 | — | 0 | 14.2 | 4.51 | 54.9 |

TABLE-continued

| Example No. | Temp. °C. | Pressure psig | Initiator | Initiator Amount[1] | CCl$_4$ wt %[2] | Cl$_2$ mole %[3] | CH$_2$Cl$_2$/CH$_2$Cl$_3$[4]* |
|---|---|---|---|---|---|---|---|
| 5 | 100 | 490 | — | 0 | 20.8 | 7.30 | 42.5 |
| 6 | 110 | 545 | — | 0 | 25.4 | 9.50 | 31.1 |
| 7 | 110 | 475 | — | 0 | 35.6 | 15.80 | 16.0 |
| 8 | 130 | 440 | — | 0 | 65.5 | 7.90 | 39.0 |
| 9 | 160 | 505 | — | 0 | 75.6 | 11.30 | 22.1 |
| 10 | 175 | 590 | — | 0 | 79.6 | 10.90 | 24.6 |
| 11 | 160 | 510 | — | 0 | 80.0 | 11.15 | 25.9 |
| 12 | 160 | 540 | — | 0 | 77.3 | 15.00 | 15.3 |

*100% Cl conversion
[1] measured as ppm based on the available chlorine
[2] measured on basis of total weight of CCl$_4$, Cl$_2$ and CH$_3$Cl initially in reaction mix
[3] measured on basis of moles Cl$_2$ and CH$_3$Cl initially in reaction mix
[4] measured ratio on weight basis
[5] azobisisobutyronitrile The figure graphically shows a plot (B—B) of the results in the Table and a plot (A—A) of standard results from a gas phase chlorination scheme. As can be seen from the plots, plot A—A yields a weight ratio of CH$_2$Cl$_2$ to CHCl$_3$ ranging from 6 to 26 while plot B—B has weight ratios within the range of from 12 to 115 for the same mole percent chlorine fed. In fact, for the same mole percent chlorine fed, plot B—B shows at least about twice the preference for methylene chloride production than that for plot A—A.

The following illustrates the method of calculation for converting the mole percent of chlorine used in the above table to mole ratio of chlorine to methyl chloride used in the claims.

To convert, mole % of Cl defined as $$\frac{\text{moles Cl}_2 \times 100}{\text{moles Cl}_2 + \text{moles CH}_3\text{Cl}}$$

to the mole ratio of Cl:CH$_3$Cl use as a basis, 1 mole of CH$_3$Cl and use moles Cl$_2$ = x and apply $$\frac{(x)(100)}{x+1} = \text{mole \% Cl}.$$

To change mole % Cl to mols Cl, divide both sides of the equation by 100 to give, $$\frac{x}{x+1} = \frac{\text{mole \% Cl}}{100}$$

From Table, Example No. 4:

$$\frac{x}{x+1} = \frac{4.51}{100} = 0.0451$$

therefore x = 0.0451x + 0.0451
x = 0.047 = moles Cl and thus, the mole ratio of Cl:CH$_3$Cl is 0.047:1 in accordance with basis of 1 mole of CH$_3$Cl.

We claim:

1. A process for the production of methylene chloride by the liquid-phase chlorination of methyl chloride, which process comprises the steps of:
    (a) forming an uninitiated liquid-phase reaction mixture containing chlorine and methyl chloride, the mole ratio of chlorine to methyl chloride lying between about 0.047:1 and about 0.079:1;
    (b) holding the reaction mixture in a closed vessel under a pressure within the range of from about 100 to about 800 psig, and at a temperature within the range of from 40° C. to about 175° C. during the reaction period; and
    (c) recovering the methylene chloride formed.

2. The process of claim 1 wherein said chlorine is provided to said reaction mix as gaseous chlorine which is solubilized in the liquid methyl chloride in the reaction mixture.

3. The process of claim 1 wherein said uninitiated liquid-phase reaction mixture consists essentially of chlorine and methyl chloride.

4. The process of claim 1 wherein said reaction mixture consists of chlorine and methyl chloride.

5. The process of claim 1 wherein said chlorine portion of said reaction mixture is introduced thereto by sparging gaseous chlorine into the methyl chloride portion of said reaction mixture.

* * * * *